United States Patent
Biermann et al.

(10) Patent No.: US 7,464,531 B2
(45) Date of Patent: Dec. 16, 2008

(54) METHOD FOR VISUALLY DISPLAYING THE MAINTAINING OF SPECIFIED EFFECTS

(75) Inventors: Iris Biermann, Mönchengladbach (DE); Christoph Haase, Viersen (DE); Lorenz Kreitzen, Rheinberg (DE)

(73) Assignee: Oerlikon Textile GmbH & Co. KG, Remscheid (DE)

( * ) Notice: Subject to any disclaimer, the term of this patent is extended or adjusted under 35 U.S.C. 154(b) by 16 days.

(21) Appl. No.: 10/575,688

(22) PCT Filed: Sep. 10, 2004

(86) PCT No.: PCT/EP2004/010141

§ 371 (c)(1), (2), (4) Date: Mar. 27, 2007

(87) PCT Pub. No.: WO2005/042815

PCT Pub. Date: May 12, 2005

(65) Prior Publication Data

US 2007/0277495 A1   Dec. 6, 2007

(30) Foreign Application Priority Data

Oct. 16, 2003   (DE) ................................. 103 48 741

(51) Int. Cl.
*D01H 13/10*   (2006.01)

(52) U.S. Cl. .......................................................... 57/264
(58) Field of Classification Search ................... 57/264, 57/265

See application file for complete search history.

(56) References Cited

U.S. PATENT DOCUMENTS

| | | | | |
|---|---|---|---|---|
| 5,537,811 A * | 7/1996 | Pidoux et al. | .................. | 57/264 |
| 5,832,709 A * | 11/1998 | Lassmann et al. | ............. | 57/263 |
| 6,798,506 B2 * | 9/2004 | Furter | ...................... | 356/238.2 |
| 2003/0037531 A1 * | 2/2003 | Eaton | ........................... | 57/265 |

* cited by examiner

*Primary Examiner*—Shaun R Hurley
(74) *Attorney, Agent, or Firm*—K & L Gates LLP

(57) ABSTRACT

A method for visually displaying the maintaining of specified effects in a produced fancy yarn by measuring the deviations of the yarn diameter from the desired specifications. The display is a two-dimensional classifying matrix which is known per se. The display matrix is divided into longitudinal regions in one dimension and diameter regions in the other dimension, and forms a class in each case by combining a longitudinal region with a diameter region, wherein each deviation from the desired specification is allocated to a class. Only the effect regions of a fancy yarn are included in the classifying matrix, with only the regions of the fancy yarn counting as effect regions, the diameter of which is at least a specified amount over a specified web diameter and the length of which exceeds a specified minimum length.

6 Claims, 1 Drawing Sheet

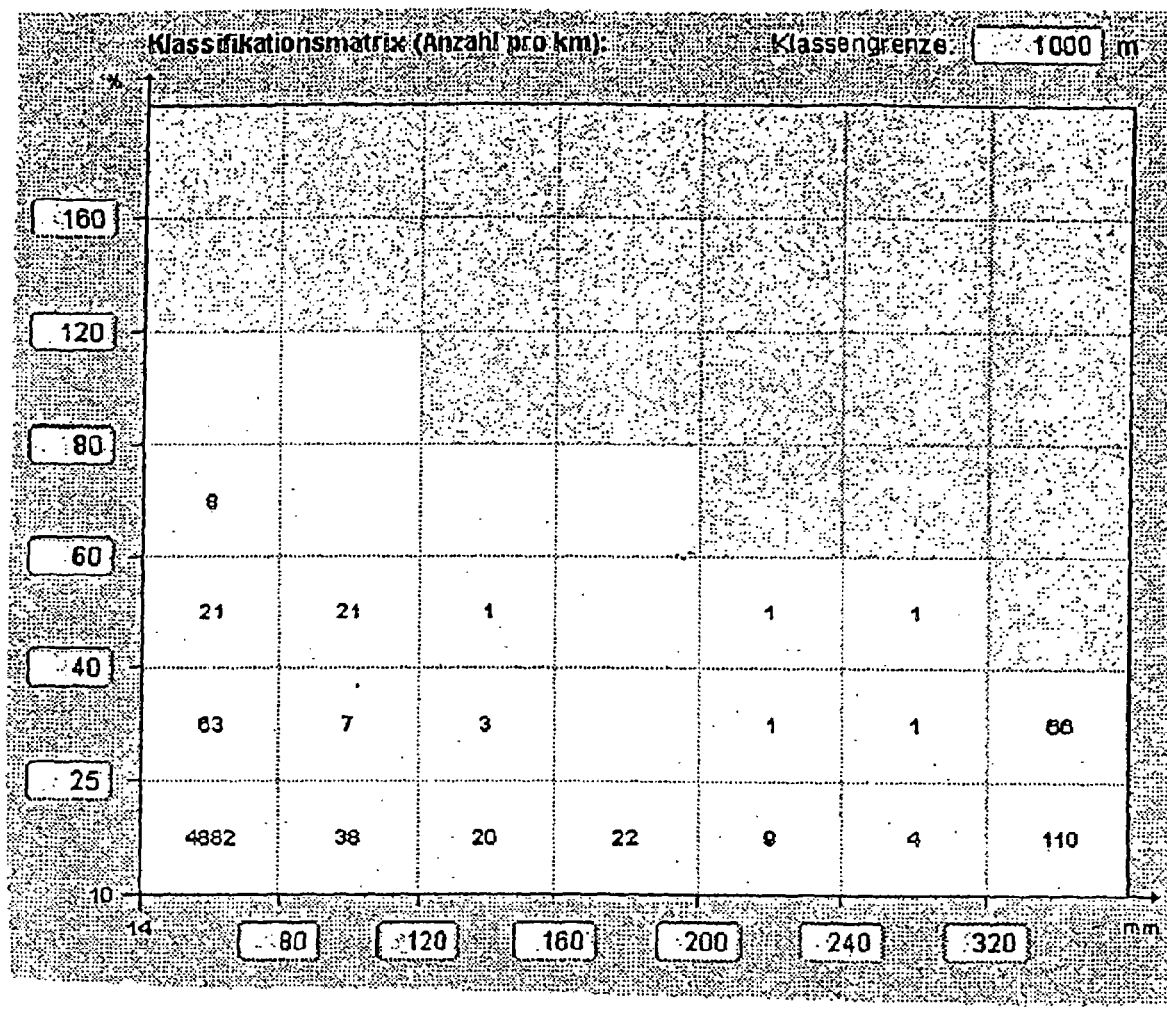

METHOD FOR VISUALLY DISPLAYING THE MAINTAINING OF SPECIFIED EFFECTS

CROSS-REFERENCES TO RELATED APPLICATIONS

This application claims the benefit of German patent application 103 48 741.7, filed Oct. 16, 2003, herein incorporated by reference.

BACKGROUND OF THE INVENTION

The invention relates to a method according for visually displaying the maintaining of specified effects in a produced fancy yarn and, more particularly, relates to such a method accomplished by measuring the deviations of the yarn diameter from the desired specifications.

To produce fancy yarn, the desired configuration of the yarn is established and the spinning adjustments required to spin the fancy yarn are generated on the basis of establishing this configuration. For this purpose, the effects, characterized by the effect thickness and effect length, and webs, characterized by the web thickness and the web length, and the sequence of webs and different effects are specified. This specification is stored in a so-called pattern repeat and can be shown, for example, as a virtual yarn table on a screen. A display of this type is not, however, adequately significant in the case of a visual check in order to be able to quickly and clearly recognize whether the specified effects are present in the specified distribution in the fancy yarn produced.

SUMMARY OF THE INVENTION

The object of the invention is to provide a method, with which the check as to whether the specified effects have been produced as desired in the fancy yarn produced can be improved.

This object is achieved by a method for visually displaying the maintaining of specified effects in a produced fancy yarn by measuring the deviations of the yarn diameter from the desired specifications. According to the invention, the display, a two-dimensional classifying matrix known per se is used. The display matrix is divided into longitudinal regions in one dimension and diameter regions in the other dimension, and forms a class in each case by combining a longitudinal region with a diameter region, wherein each deviation from the desired specification is allocated to a class. Only the effect regions of a fancy yarn are included in the classifying matrix, with only the regions of the fancy yarn counting as effect regions, the diameter of which is at least a specified amount over a specified web diameter and the length of which exceeds a specified minimum length.

The method according to the invention provides information concerning in which length and thickness classes the effects are located, and in what number. From this it can be immediately and clearly derived whether the effects have been produced in the desired configuration and number. The method makes a visual evaluation possible and also automatic evaluation. A simple evaluation can take place by a DESIRED/ACTUAL comparison, in which the number of effects actually present and shown accordingly in the classifying matrix is compared with the provided number of effects in the respective class. The introduction of measures can be made dependent on a specific degree of coincidence or the difference between the shown number of effects and the provided number of effects. By means of different colored backgrounds of the classes, in which effects are provided and of the classes, in which no effects are provided, a visual check can be carried out more easily and quickly. Optimization of the spinning adjustments can be triggered on the basis of the display of the classifying matrix.

BRIEF DESCRIPTION OF THE DRAWING

Further details of the invention can be found in the FIGURE. The FIGURE shows a classifying matrix for yarn effects, in which seven diameter regions of effects are shown in one dimension and seven longitudinal regions of effects are shown in the other dimension, which together form 49 classes.

DESCRIPTION OF THE PREFERRED EMBODIMENT

As noted, the FIGURE shows a classifying matrix for yarn effects, in which seven diameter regions of effects are shown in one dimension and seven longitudinal regions of effects are shown in the other dimension, which together form 49 classes. The first diameter region extends from one diameter value, which is 10% above the web diameter up to a diameter value, which is 25% above the web diameter. The first longitudinal region extends from 14 mm to 80 mm. In the class formed by these two regions, 4,882 effects have been determined over 1,000 meters of yarn length. The distribution of the effects determined over the individual classes can be inferred from the representation of the FIGURE. The sums shown in the individual classes relate to 1,000 meters of measuring length. If a smaller measuring length is recorded, the results are calculated up to 1,000 meters. In addition, the sum of the effects in all classes of a longitudinal region or the sum of all the effects in the classes of a diameter region can be shown. Rapid and simple checking as to whether the effect specification is being maintained is possible with the sums shown in the classifying matrix.

The limits of the longitudinal regions and the thickness regions can be changed in a freely selectable manner. The classifying matrix of the FIGURE shows a region, in which the classes have a white background and another region—in the view of the FIGURE at the top right—which has a grey background. The classes with white backgrounds represent classes, in which the effects should be found. The classes with grey backgrounds represent the other regions. For example, if the desired effect configuration only comprises effects, in which the effect thickness in each case is at least 25% above the web thickness, in the corresponding classifying matrix, not shown here, the seven classes of the thickness region from 10% to 25%, which have white backgrounds in the lower row of the view of the FIGURE, now no longer have white backgrounds, but grey. If, in these classes with grey backgrounds, effects are shown, it is obvious that the fancy yarn does not contain specified effects. The showing of effects in the classes with grey backgrounds can trigger an optimization of the spinning adjustments with the aim of eliminating these undesired effects in future in the production of the fancy yarn.

The classifying matrix can be displayed on a screen or by print-out.

The invention is not limited to the classifying matrix shown. In the scope of the invention, further configurations of the classifying matrix are possible.

The invention claimed is:

1. A method of producing a visual display of actual effects measured in a fancy yarn, wherein the fancy yarn comprises a lengthwise alternating series of webs of relatively smaller diameter and effects of relatively larger diameter, wherein said display comprises a two-dimensional x-y tabular classifying matrix presenting a grid of multiple classes which classify in one x-y direction according to graduated values of measured quantities representing effect diameter and which classify in the other x-y direction according to graduated values of measured quantities representing effect length, each class displaying a respective numerical sum total of the incidence of said measured effects in a defined length of yarn according to said graduated values compared to desired specifications, wherein said display presents said numerical sums for only said effect regions having diameters exceeding a predetermined minimum diameter value and having lengths exceeding a predetermined minimum length value.

2. The method according to claim 1, wherein the predetermined minimum diameter value is at least 10% above the diameter of said webs.

3. The method according to claim 1, wherein the predetermined minimum length value is a length of 14 mm.

4. The method according to claim 1, wherein the defined length of yarn is 1,000 meters of yarn length.

5. The method according to claim 1, wherein the graduated values in the respective x-y directions can be selectably changed.

6. The method according to claim 1, wherein the grid of the classifying matrix presents seven graduations in each of the x and y directions.

* * * * *